United States Patent
Spink et al.

[11] Patent Number: 5,953,114
[45] Date of Patent: Sep. 14, 1999

[54] METHOD OF DETERMINING MEASUREMENT-POINT POSITION DATA AND DEVICE FOR MEASURING THE MAGNIFICATION OF AN OPTICAL BEAM PATH

[75] Inventors: Roger Spink, Balgach; Bernhard Braunecker, Rebstein; Klaus-Peter Zimmer, Heerbrugg, all of Switzerland; Thomas Mayer, Hohenems, Austria; John Rice Rogers, Heerbrugg, Switzerland

[73] Assignee: Leica Mikroskopie Systeme AG, Heerbrugg, Switzerland

[21] Appl. No.: 08/722,019
[22] PCT Filed: Apr. 9, 1995
[86] PCT No.: PCT/EP95/01311
  § 371 Date: Dec. 11, 1996
  § 102(e) Date: Dec. 11, 1996
[87] PCT Pub. No.: WO95/27918
  PCT Pub. Date: Oct. 19, 1995

[30] Foreign Application Priority Data

Apr. 11, 1994 [CH] Switzerland ............ 1088/94
Apr. 11, 1994 [CH] Switzerland ............ 1089/94
Apr. 11, 1994 [CH] Switzerland ............ 1090/94
Apr. 11, 1994 [CH] Switzerland ............ 1091/94
Apr. 11, 1994 [CH] Switzerland ............ 1092/94

[51] Int. Cl.⁶ ............ G01B 9/02; G02B 21/22; A61B 3/10
[52] U.S. Cl. ............ 356/152.1; 359/377; 351/212
[58] Field of Search ............ 356/152.1, 376, 356/124; 250/561; 349/79, 86

[56] References Cited

U.S. PATENT DOCUMENTS 4,787,734  11/1988  Matsumura ............ 356/124
5,073,857  12/1991  Peters ............ 364/413.1
5,345,087   9/1994  Luber et al. ............ 356/152.1

FOREIGN PATENT DOCUMENTS

95/18511  7/1995  WIPO .
95/18512  7/1995  WIPO .
95/27226  10/1995  WIPO .

*Primary Examiner*—Frank G. Font
*Assistant Examiner*—Roy M. Punnoose
*Attorney, Agent, or Firm*—Foley & Lardner

[57] ABSTRACT

The invention relates to a method of determining measurement-point position data and a device for measuring the magnification of an optical beam path. In the method described, a laser beam is inserted via an insertion element (32a) into the beam path of a microscope. At the end of this beam path, a beam splitter (4c) splits the laser beam off again and directs it on to a position sensor (45a). The point at which the measurement beam is incident depends on the magnification of the beam path optics (8, 13). The final value of the magnification can thus be simply determined. The value of the magnification is important for the user in order to enable the user to make a definite assessment of the area observed. Also described are various related developments and details of the invention.

16 Claims, 12 Drawing Sheets

METHOD OF DETERMINING MEASUREMENT-POINT POSITION DATA AND DEVICE FOR MEASURING THE MAGNIFICATION OF AN OPTICAL BEAM PATH

BACKGROUND

The invention relates to a method of determining position data of a measurement point and a device for measuring the magnification in an optical beam path, in particular in a beam path of a surgical microscope.

Surgical microscopes are used by a surgeon for the optical magnification of the area in which an operation is intended to be carried out. There are in principle three different types of surgical microscopes, all of which are meant in the sense of the invention. These are, firstly pure optical microscopes, that is to say microscopes which contain only optical and mechanical components, the output being directed to the eye;

secondly pure video microscopes, that is to say microscopes which have optical, mechanical and optoelectronic components, the optical output of the microscope being directed exclusively to an optoelectronic image recording device (for example a CCD), and the image recorded being further processed exclusively electronically and, if appropriate, being displayed via a display; and thirdly mixed video microscopes, which contain constructional features of the microscopes of the first and second type in common, that is to say that an output is directed both to an observer's eye and to an image recording device.

As a result of the magnification of the area to be operated on, a surgeon loses the direct estimation of size which he/she has in the case of operations with the unaided eye. This leads to problems primarily where specific, previously determined cut depths or cut lengths are to be observed, or where the surgeon has to keep to specific distances using a surgical tool in order to make a precise operation possible. Above all in the case of operations on the brain or in microsurgery, this is often imperative in order to avoid damage to healthy tissue. In the case of such operations, the result of the operation (whether complete success or death) often depends on fractions of millimeters. Therefore, efforts have been made to determine the areas as precisely as possible and to permit measurements of sizes. As an example of such a known construction, reference is made to the German Patent Application DE-A-4134481.

In the DE-A mentioned, a surgical microscope is described in which an exact location determination is intended to be carried out of a specific point, generated by means of a laser beam, on an object being observed. For this purpose, a sighting method is proposed in which, by means of focusing and defocusing the microscope, respectively, visual field markings are brought into coincidence. After this, the exact determination of the position of the point on the object is intended to be possible, in that optical system data are used for calculation. These system data are intended to be determined, according to the DE-A, by means of suitable distance detectors or angle detectors on drive units for the respective positioning of positionable optical components. It is specifically intended to draw conclusions therefrom about the magnification of the magnification system.

The determination of the magnification is therefore carried out indirectly via the measurement of distances, angles or via sensors which are connected to positioning devices for optical components, and via a subsequent calculation of the corresponding data.

This is in many cases unsatisfactory and insufficient. The main reason lies in the fact that both the optomechanical components and the mechanical/electrical components (sensors) have tolerances which, under certain circumstances, change nonlinearly. This results in the risk that magnification values determined in this way are wrong and therefore the position data further determined therefrom are not correct. In the extreme case, such incorrect data could lead to serious errors during the work of the surgeon. Such errors are possibly somewhat lessened by—necessarily provided in accordance with the DE-A—calibration measurements on the patient. However, even these are not indisputable and depend primarily on the human capability of the operator. The known attempt to register mechanical tolerances of the magnification system during the assembly of the microscope and to determine therefrom a correction curve, which is superimposed onto the current data, is insufficient to the extent that tolerances may change as a function of countless factors, and the correction curves then used are of no help. In addition, the determination of such correction curves is itself problematic, above all time-consuming. A corresponding correction program, furthermore, requires additional computing power and, in some cases, reduces the computer speed in the real time area.

SUMMARY OF THE INVENTION

The invention is therefore based on the object of developing a method in which the said disadvantages are avoided and position data can be determined rapidly and reliably. This object is achieved, for example, by the fact that, during the determination of position data, the magnification of the microscope is in each case measured directly and while avoiding use of mechanical elements or mechanical sensors. The measured value can then be used, for example in the context of known systems or methods, for example in accordance with the said DE-A, instead of the value determined by roundabout ways, for calculating the position data. Apart from this, such an actually measured magnification value can also be immediately directly used in the—for example electronic or software-aided—magnification change of any other image data such as, for example, MRI or X-ray image data, should such image data be superimposed on the image data determined from the microscope with the aid of a known or new system.

With regard to the method for determining position data, reference is made in particular to the description parts of the mentioned DE-A, which count as disclosed within the scope of this description. These are in particular: column 2 line 13 to column 4 line 5, and FIGS. 2–4 and the associated description parts. With regard to the possibility of superimposing image data, reference is additionally made to the following Swiss Patent Applications, whose corresponding description passages and figures also count as disclosed within the scope of this application. These are the applications: CH135/94-3; CH198/94-5; CH949/94-2; CH1090/94-1; CH1091/94-3; CH1092/94-5; CH1525/94-0; CH3890/93-3.

Moreover, the invention is furthermore based on the somewhat more general object of providing a device with which the magnification (positive or negative) can be measured directly in a beam path having optical components, in particular in a microscope. The measurement data should serve for the calculation of position data or else also merely for the information of the operator.

This object is achieved, for example, by means of the features described below.

The application of the described features leads to a simple construction which impairs the optical properties of the microscope very little. As a consequence of the small diameter of a measuring beam, which is preferably constructed as a laser beam, an insertion element can be constructed to be very small. Furthermore, it can be arranged in the direct vicinity of the main objective, with the result that it lies optically below the perceptibility limit. Known optical sensors such as diode arrays, CCDs, etc. can be considered as the measuring array, in principle a linear extent of the array being sufficient. In principle, all reflective components are considered as the insertion element, such as beam splitters, mirrors, reflective prism surfaces, etc.

One of the two solutions mentioned and also to be applied independently of another objective results from the application of a flat glass disk as a carrier plate for the insertion elements. Such a carrier plate makes it possible to minimize the relevant optical components in terms of their constructive size and to lead them as close as possible to the main objective. The assembly in the mechanical construction of such components and their fastening device, respectively, also becomes particularly simple thereby.

According to a special embodiment of the invention, that part of the measuring beam which passes through the beam splitter for splitting out the measuring beam is filtered out by means of a narrow band filter, or the measuring beam is selected in a frequency range such that it remains hidden from the human eye.

The invention can be applied in all the above-mentioned types of microscopes, in the case of video microscopes the resulting image point also being able to be removed electronically on the image recording device (e.g. on the CCD). On the other hand, the image recording device itself could replace the measuring array, if it is possible to represent the measuring point of the measuring beam resulting therefrom with sufficient contrast and without disturbing the surgeon—for example split out electronically.

The measuring beam transmitting frequency, which is reduced in accordance with a development according to the invention, reduces any stress on a human eye in another way, without impairing the measuring accuracy. If required, such a device can also be clocked or synchronized with the image recording device and with any reference arrays, etc., in order to exhibit the optimum efficiency with the lowest interference. Thus, for example, the measuring beam can always be emitted just when the image recording device is not ready for the reception of image data. Since the magnification—in the case of a fixed setting of the main objective—as a rule changes only as a result of changing the zoom setting, it may be advantageously sufficient if the measuring beam in each case is emitted only directly following a change of setting on the zoom—which can be determined by a pick off on the servomotor of the zoom.

A further development of the invention, which can also be used independently, if required, provides for a mechanical magnification indicator which is coupled to the positioning device, for example for a zoom, any nonlinearities in the positioning of the optical components being compensated by means of a cam disk.

The invention is described in particular in conjunction with a surgical microscope. In the widest sense, however, it can also usefully be applied with any other beam paths.

Within the context of the invention, there are various further methods, types of embodiments and variants thereof, which are identified or described in below and in the figures. Furthermore, following study of this application and of the documents cited herein, different combinations of the most diverse features of constructions which are not directly described herein, and which likewise lie within the context of the invention, are evident to those skilled in the art.

BRIEF DESCRIPTION OF THE DRAWINGS

Further details and embodiments of the invention emerge from the drawings, wherein.

The figures are described coherently. Identical reference symbols denote identical components. Identical reference symbols with different indices denote similar or functionally similar components. The invention is not restricted to the exemplary embodiments shown. Above all, in combination with the teachings of the Swiss Patent Applications listed above and the German Patent Application listed above, further arbitrary variants may be shown. They all fall under the disclosure content of this application.

DETAILED DESCRIPTION OF PREFERRED EMBODIMENTS

Figure 1:
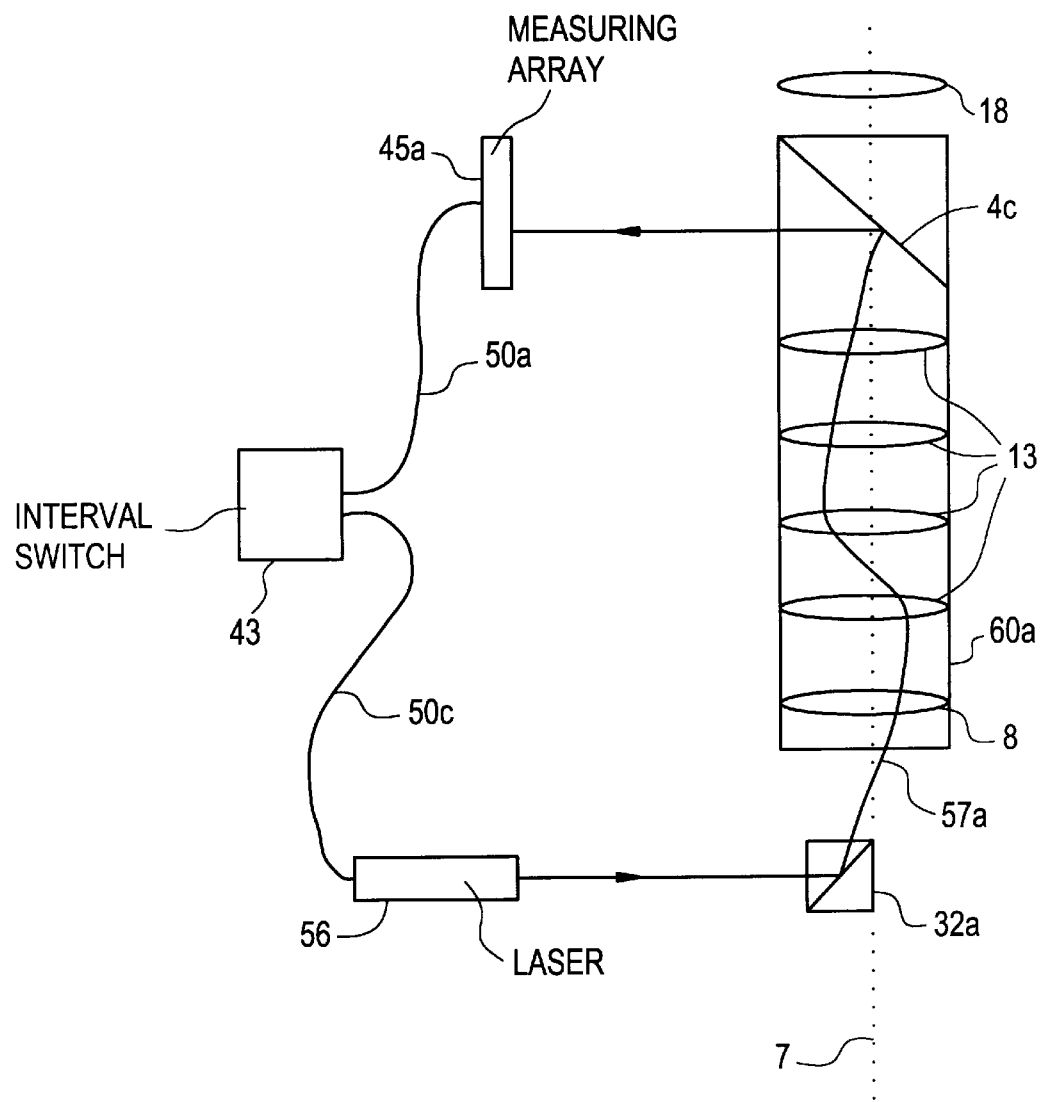
FIG. 1 shows the principle of a construction according to the invention for measuring the magnification of a microscope beam path.

FIG. 1 shows a beam path 60*a* with a schematically indicated main objective 8 and a zoom 13. Upstream of the main objective 8, to the side of the optical axis 7 of the beam path 60*a*, a small beam splitter 32*a* is adjustably arranged as an insertion element. The mounting of the beam splitter is not shown, since a multiplicity of suitable mountings are known to those skilled in the art. Facing the input side of the beam splitter 32*a* is a laser 56, which directs a measuring beam 57*a* onto the beam splitter surface. This is preferably aligned in such a way that the split off beam 57*a* runs at an angle to the axis 7. The beam passing through forms a reference beam, which is assigned to a reference array.

Arranged downstream of the beam path 60a is a beam splitter 4c for splitting out the measuring beam 57a. Its output faces a location-resolving optoelectronic measuring array 45a, at which the split out beam 57a is intercepted.

The measuring principle according to the invention lies in the fact that the measuring beam 57a reflected in upstream of the main objective 8 arrives at a specific place on the measuring array 45a as a function of the magnification in the beam path 60a, said measuring array being able to be electronically interrogated and correspondingly evaluated.

Since, in the case of this construction, that component of the measuring beam 57a which passes in a straight line in the beam splitter 4c can fall through the eyepiece 18 into an observer's eye, provision is made here for the beam 57a to be emitted only occasionally. An interval switch 43 which is connected via a connecting line 50a to the measuring array 45a and via a connecting line 50c to the laser 56, interrupts the beam emission from the laser 56 continuously, so that the measurements are carried out only from time to time. This is important when the measuring beam 57a is either so bright that it disturbs an observer, or that its power in the infrared range is so intense that damage can occur at the observer's eye under permanent irradiation.

Figure 2:
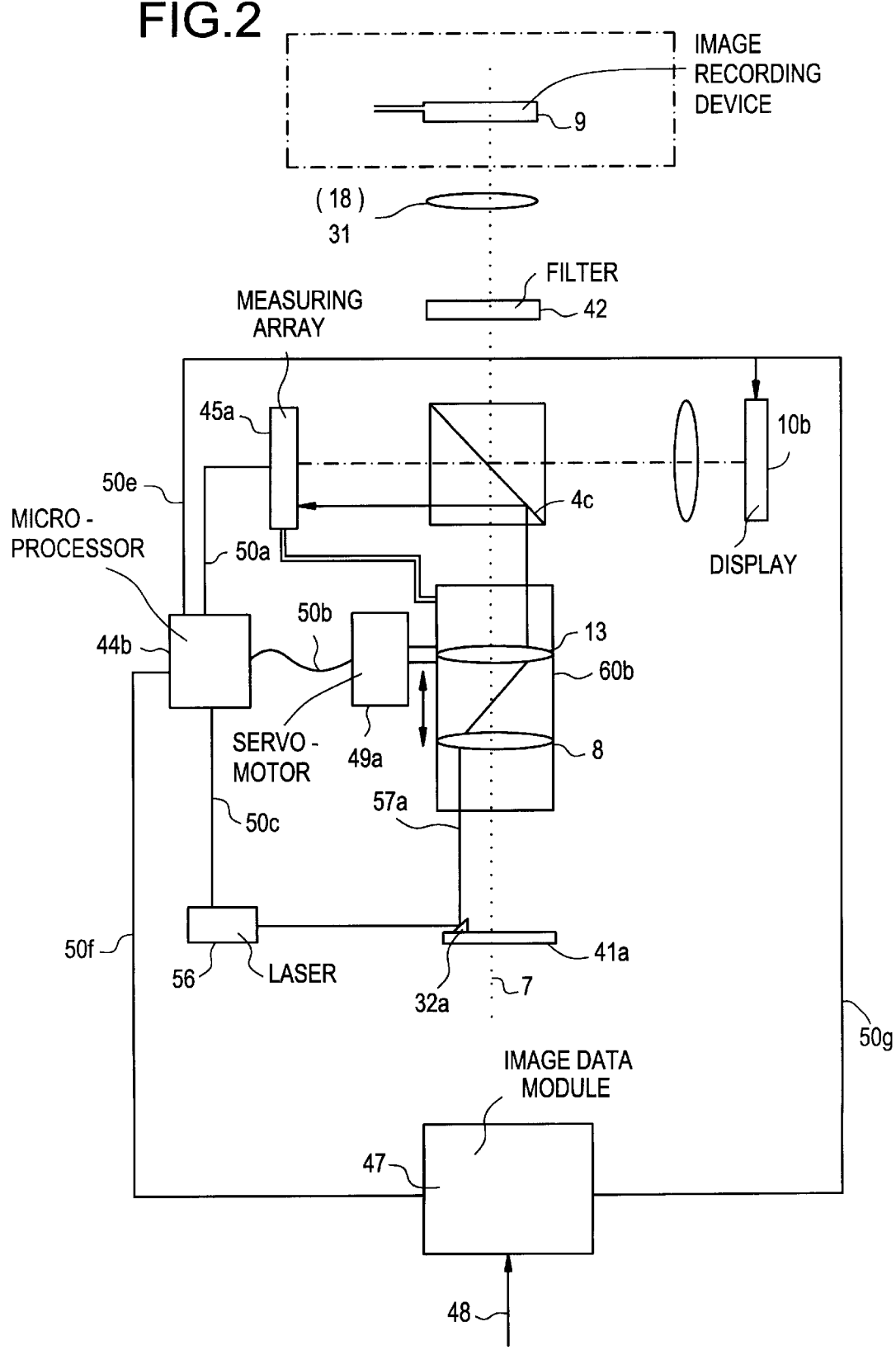
FIG. 2 shows the principle of a variant of the construction according to FIG. 1 with a conventional display for reflecting in magnification information and/or other image data.

FIG. 2 is different to the extent that, in addition to the components described, a servomotor 49a is provided for the zoom 13, and is likewise connected via a connecting line 50b to a microprocessor 44b. This connection enables measurements to be reduced to an absolute extent, namely to those cases in which a setting change has been undertaken by the zoom 13. Disturbances to an observer's eye are thereby minimized.

By means of a color filter 42, which is arranged downstream of the beam splitter 4c, disturbances for an observer's eye can be completely eliminated. The filter is preferably of a very narrow band character and just filters out only the color wavelength of the measuring beam (which is located, for example, in the infrared range).

The eyepiece 18 could alternatively also be a tube lens for an image recording device 9, which can be provided either instead of an observer's eye or, via known arrangements, can also be fitted in addition thereto—for example split out via a further beam splitter.

In the case of this special refinement, the beam splitter 4c is also used as an insertion part for the image of a display 10b, on which image data from a module 47 for image data transmission can be displayed. These are as a rule X-ray image data, MRI image data, or else other information such as medical values relating to the patient, position values of the microscope or else just magnification values of the microscope, which are obtained via the measuring array 45a, if necessary following conversion by the microprocessor 44b. This information is fed to the display 10b via the connecting lines 50e and 50g. The connecting line 50f enables the forwarding of the magnification data to the module 47 for image data transmission, so that preferably standardized image data from other systems, fed in via the input 48, can be supplied, converted to the correct magnification, and sent to the display 10b. By means of this device, the superimposition of image data is especially convenient for a surgeon, since the dimensions will certainly be correct.

An insertion element 32a with which the measuring beam 57a is introduced into the microscope beam path 60b can be designed in accordance with FIG. 1 as a beam splitter. However, it can also be designed as a prism or as a mirror in accordance with FIG. 2. The insertion element 32a is as a rule fastened onto a carrier plate 41a.

Figure 3:
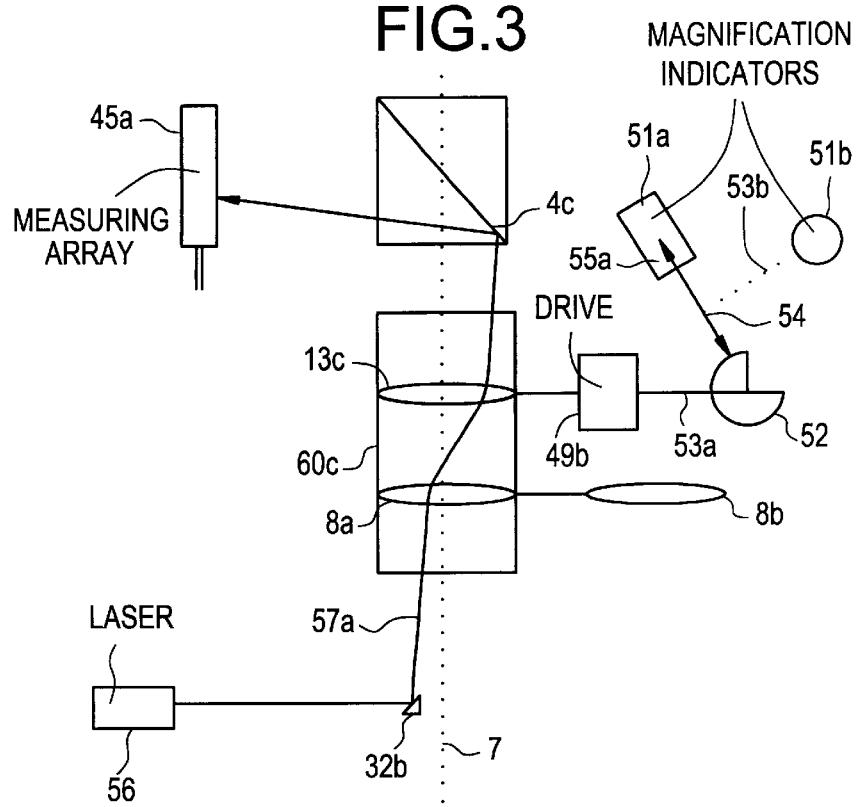
FIG. 3 shows the principle of another variant of the construction according to FIG. 1 with a novel mechanical magnification indicator.

The construction in accordance with FIG. 3 shows, as an alternative to FIG. 2, inter alia a mechanical magnification indicator which, by means of cam disk 52 passes on the mechanical positioning data of the actuating drive 49b of the zoom 13c to a pointer 55a for a magnification indicator 51a or to a disk-shaped magnification indicator 51b. For this purpose, a purely symbolic mechanical pick off 54 and a coupling 53b are indicated, which can be implemented by means of arbitrary components known to those skilled in the art. The essence of this inventive detail lies in this case in the application of the cam disk 52, which compensates for any nonlinearities occurring in the zoom positioning.

Figure 4:
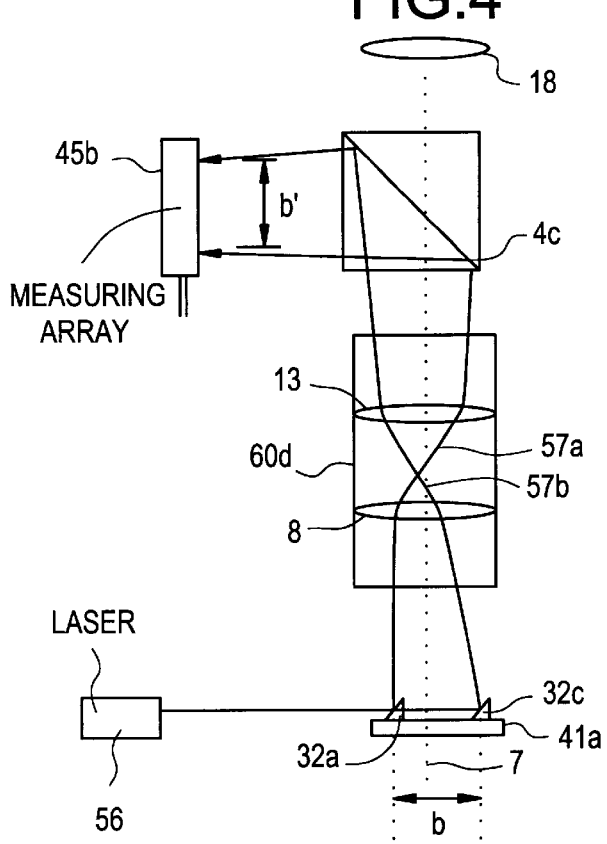
FIG. 4 shows a further variant in relation to FIG. 1 with two parallel measuring beams.

In the variant according to FIG. 4, two measuring beams 57a and 57b are transmitted through the beam path 60d at specific angles to the optical axis 7. In this arrangement, insertion element 32a is designed as a beam splitter to generate the measuring beam 57a in reflection and the measuring beam 57b in transmission and subsequent reflection at the insertion element 32c. The relation of the spacing b' measured at the measuring array 45b to the known spacing b corresponds to the magnification of the beam path 60d.

Figure 5:
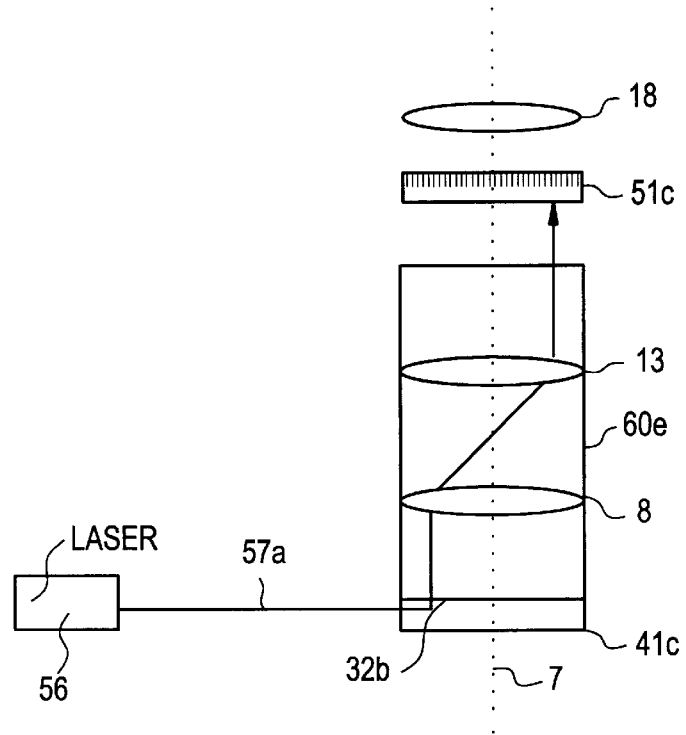
FIG. 5 shows the principle of a construction with an exclusively visual magnification indicator in the optical beam path of a microscope.

The specific variant according to FIG. 5 indicates the magnification values directly to an observer, in that a magnification indicator 51c, to which a scale is fitted, is connected downstream of the beam path 60e. The observer thus sees through the eyepiece 18 not only the observed image but also the measuring beam 57a, which moves along the calibrated measuring scale during magnification changes. It may optionally be desirable for the magnification indicator to be constructed to be at least slightly scattering in the region of the measuring scale.

Also shown in the illustration as a special feature is an alternative insertion element 32b, which essentially comprises an optionally prismatic carrier plate 41c, in which a mirror surface 32b is integrated. The carrier plate 41c is shown here as a full surface, but under certain circumstances a rod-like part, which projects only a short distance into the beam path 60e and hence leads to a minimum impairment, is sufficient.

Within the sense of the invention, it is not essential whether the specified components are arranged exactly in the sequence in which they are shown in each case. Various variations are conceivable, which may bring advantages in accordance with the desired constructional shape.

As an alternative to the described laser beams, other focused light beams are also conceivable, providing these have the same effects with regard to the focusing.

Not shown are possible filters, which are arranged directly upstream of the array 45a and the like in order to split out any interfering light from the beam path 60.

According to a further specific refinement, the beam splitter 4c could also be constructed as a beam splitter having a beam splitter surface at the Brewster angle, in order to split out a correspondingly polarized measuring beam 57 completely and to keep it away from the eyepiece 18. Such a construction is preferred where high light intensities are necessary at the measuring array 45.

Figure 7:
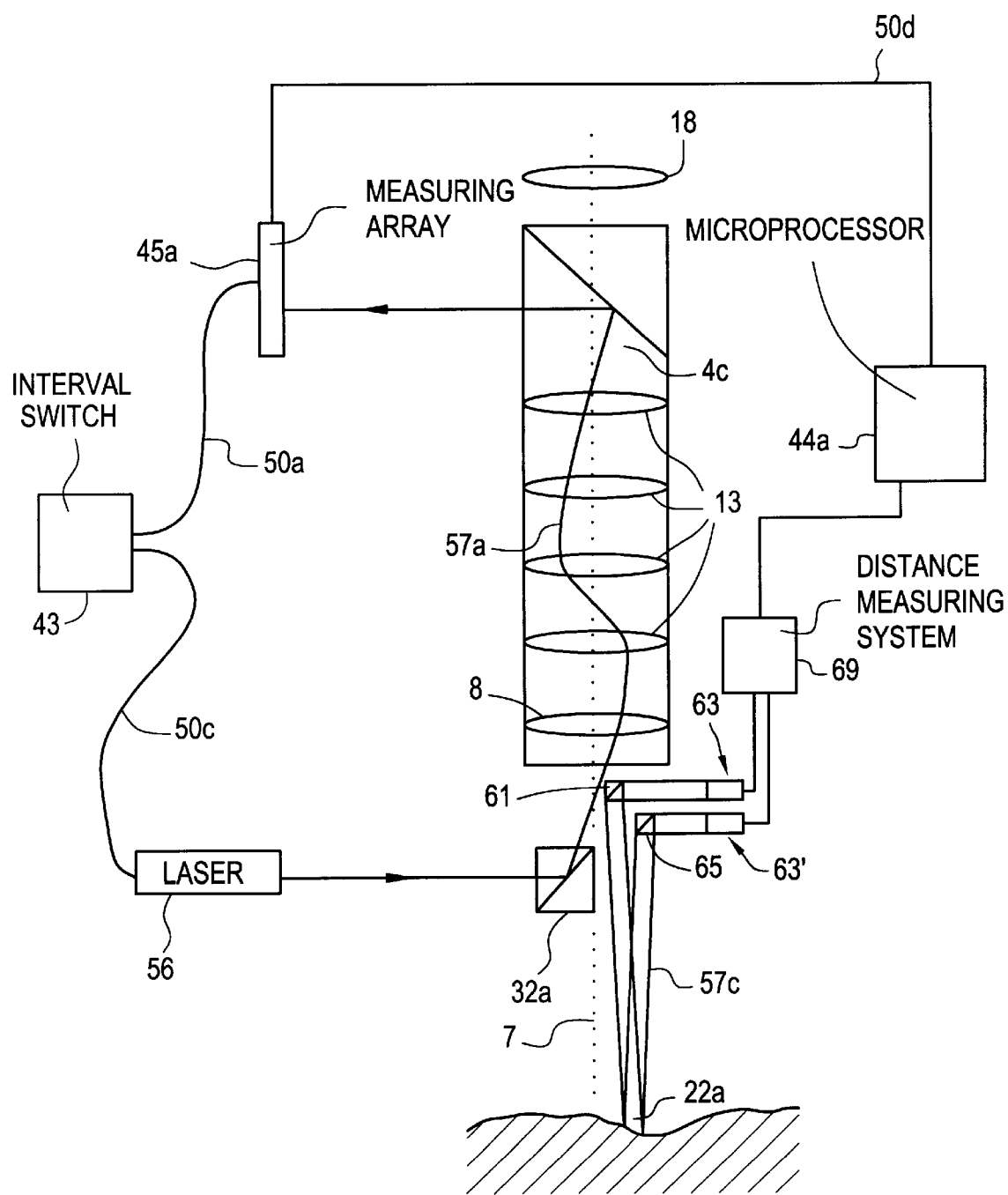
FIG. 7 shows a preferred construction, which combines the teaching according to the invention by way of example with the invention in accordance with the PCT patent application, based on CH1090/94-1.

If the teaching according to the invention is combined with the teaching of the international PCT patent application—based on the Swiss Patent Application CH1090/94-1, the result thereof is a preferred, integrated construction of a microscope. One example of such a construction is shown in FIG. 7. The statements in the said application which make reference to this example likewise count as disclosed within the scope of this application (cf. in particular claim 9 in conjunction with claims 1–8 and claims 10–15, and FIGS. 1–4 and associated description parts).

Figure 6C:
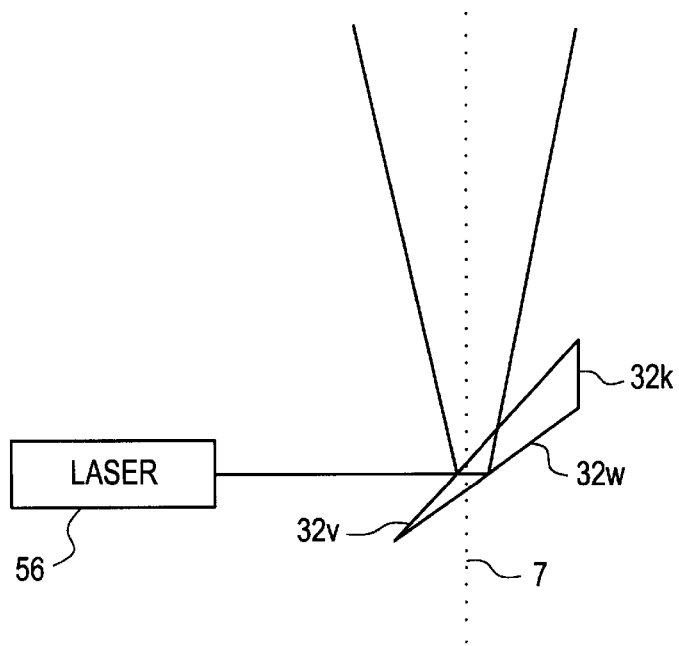
FIGS. 6A–6C show three variants of the arrangement of the insertion and splitting out elements in the beam path of a microscope.
Figure 6A:
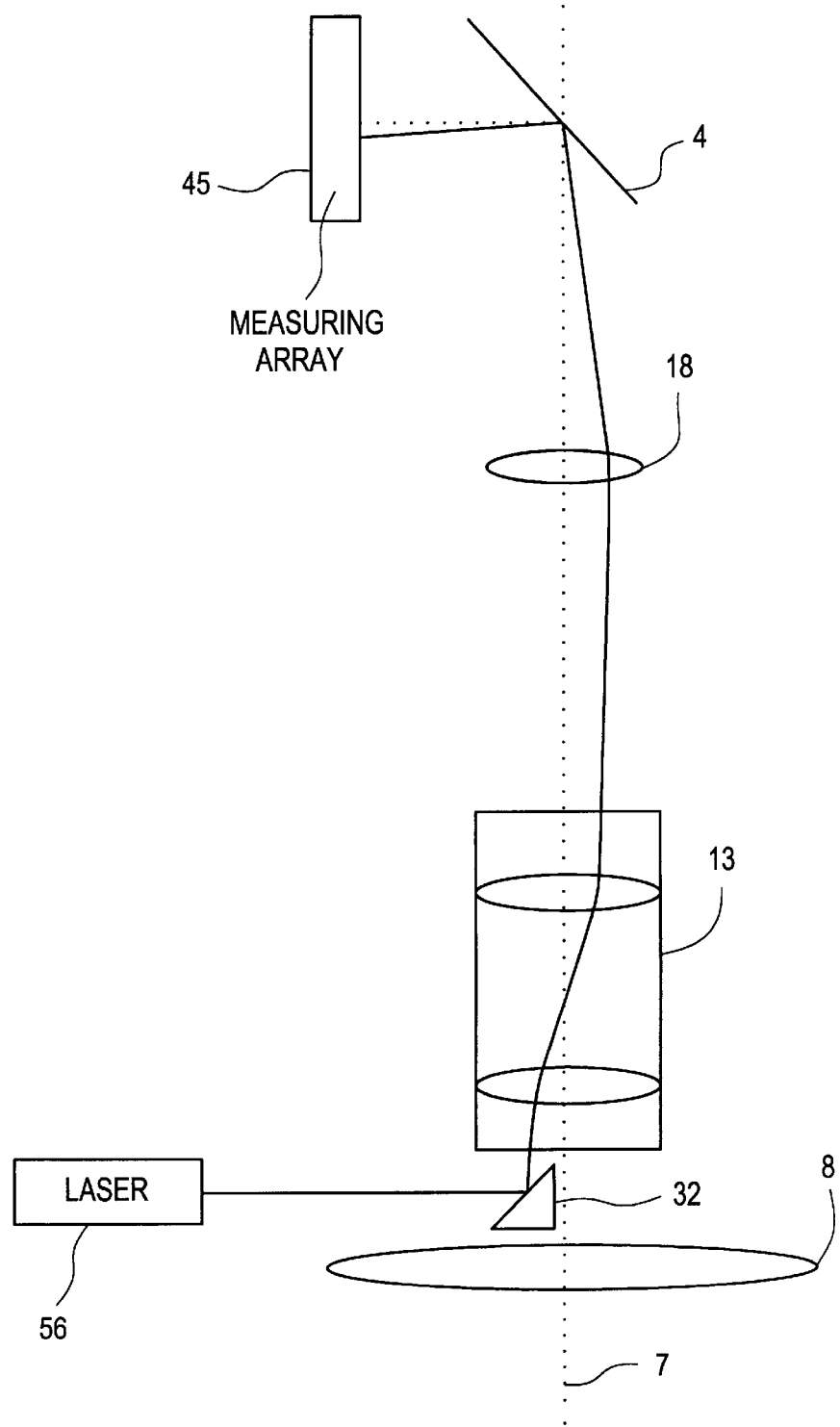

FIG. 6a shows the insertion of the measuring beam downstream of the main objective 8 via a prism 32 at an angle to the optical axis 7. Depending on the angle and the magnification, the measuring beam is incident at different locations on the sensor 45 after being coupled out by element 4.

Figure 6B:
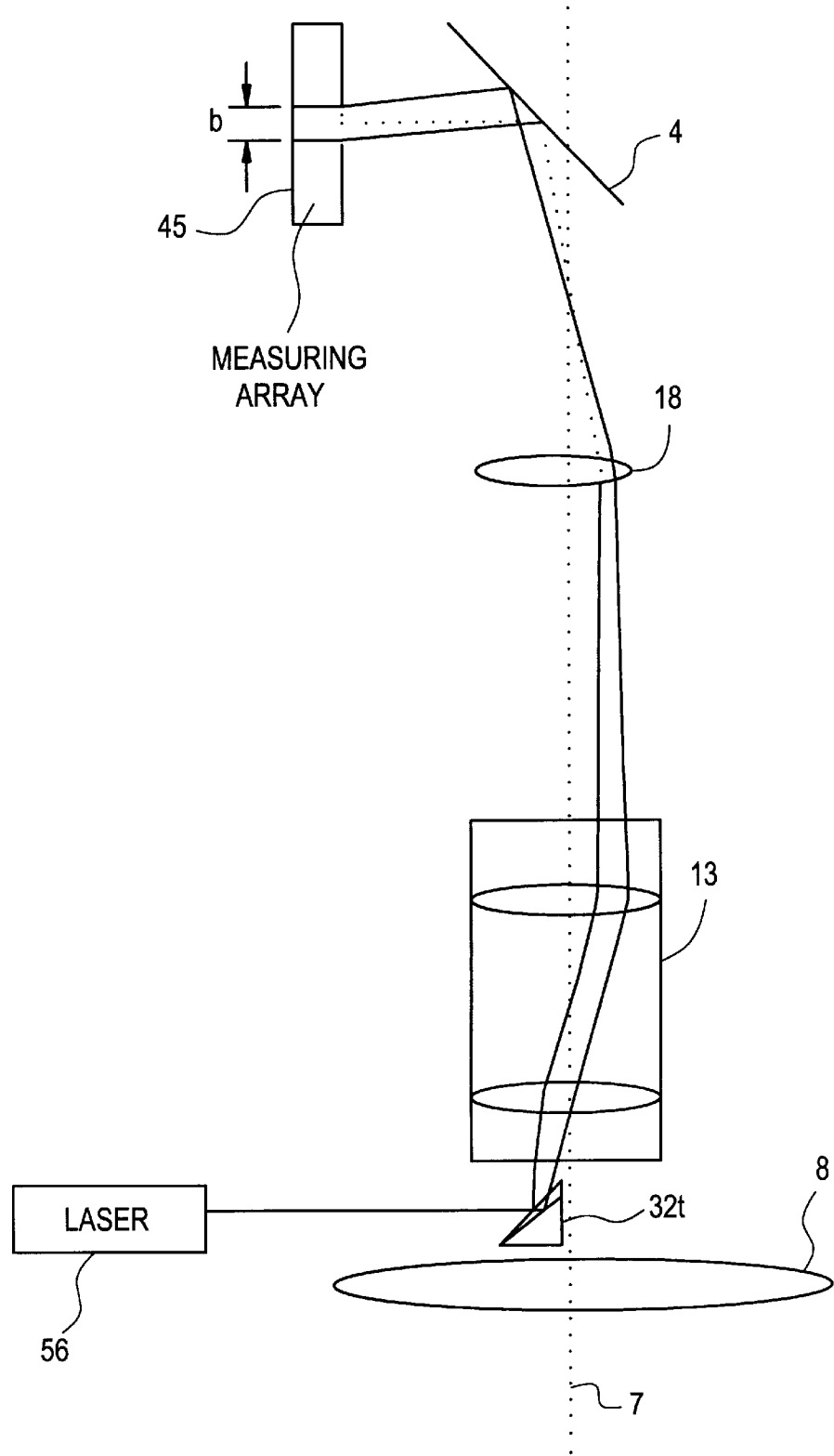

According to FIG. 6b, in order to avoid adjustment problems of the insertion element 32t, two measuring beams are produced, for example via two beam splitter surfaces which are arranged at a defined angle to each other and which produce two physically separated signals on the sensor 45.

Given a known angle, the spacing b is a measure of the magnification of the optical system. This principle may also include the main objective for determining the overall magnification, if the coupling in takes place upstream of the main objective 8.

FIG. 6c shows, as a further exemplary embodiment of an insertion element, a wedge 32k with the beam splitter surfaces 32v and 32w, for example with 4% reflectivity in each case. In this exemplary embodiment, the beam courses are selected such that they lie symmetrically with respect to the optical axis 7 following the reflections at the wedge 32k.

FIG. 7 shows a laser 56, whose beam 57a is deflected via an adjustable beam splitter 32a into the microscope optics 8, 13. From the microscope optics 8, 13 the beam 57a passes via a beam splitter 4c to a measuring array 45a. In order to determine the magnification or, respectively, the position of the focal plane, the beam positions on the measuring array 45a are used. In order to minimize possible disturbances emanating from the measuring beam, the laser 56 is controlled via an already mentioned above interval switch 43. The evaluation of the position data is carried out in a microprocessor 44a. The components described above are connected to one another by means of connecting lines 50a, c and d.

Already mentioned above distance determination is carried out via a distance measuring system 69, from which optical fibers lead to the end pieces 63 and 63'. Laser light is used, the signal 57c from which is fed in between the object and the microscope toward the first deflecting element 61. The beam reflected at the object detail 22a is deflected by the second deflecting element 65 toward the fiber-optic end piece 63' connected to the sensor. The distance measuring system 69 is connected to the processor 44a, with the result that the latter can determine real positions on the image section under examination from the distance values and the magnification values.

Figure 8:
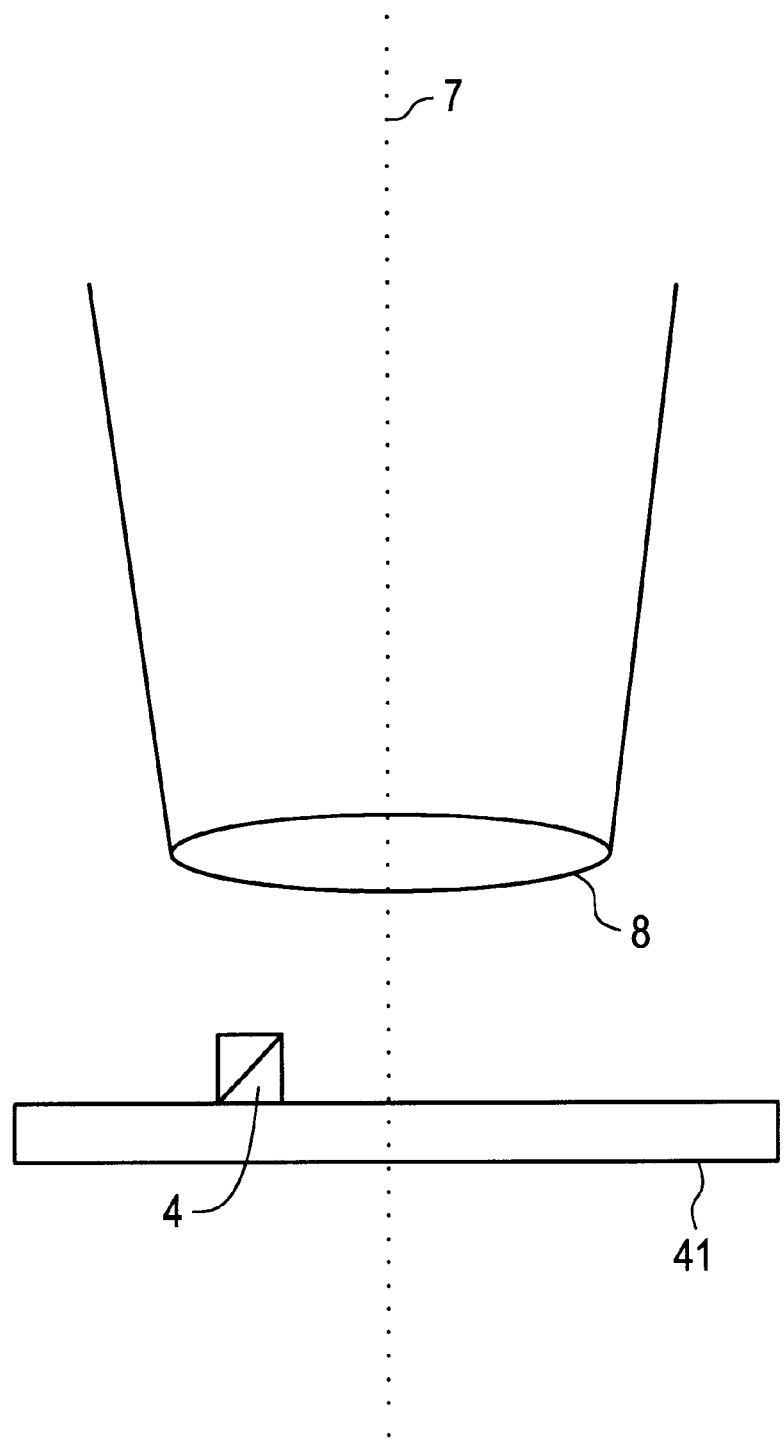
FIG. 8 shows a detail of an insertion element.

As has already been indicated in FIGS. 2, 4 and 5, the invention also relates to a device—which, if appropriate, can also be used independently—for the arrangement of insertion elements, reflecting-in elements, splitting-out elements and reflecting-out elements in an optical beam path in accordance with FIG. 8. In the area of photography and microscopy, there are often problems with the fastening of optical components for reflecting specific information into or out of an optical beam path. In the area of microscopy, there are more recent developments in which laser beams or the like have to be transmitted through the beam path.

For this purpose, beam splitters are known, which are inserted into the beam path and are shown by way of example in FIGS. 1, 3, 6 and 7. However, these enlarge the constructional volume severely and swallow light in an undesired manner.

These problems have not yet been satisfactorily solved. This aspect of the preferred refinement therefore forms the basis of the objective of providing a device which makes possible the insertion and splitting out of small ray bundles in an imperceptible manner and without severely interfering with the beam path.

Special embodiments of the invention primarily facilitate the reduction of the constructional size of surgical microscopes.

Such an arrangement therefore leads to more compact beam paths and microscopes, respectively.

Within the context of the invention, furthermore, there are various types of embodiments and variants thereof which result from the combination of the features mentioned here with features from subsequent patent applications, which place other aspects of an inventive novel microscope under protection, said microscope also being equipped precisely with the arrangement described above. These are the patent applications already mentioned. Above all, this detail is advantageous for use for magnification and distance measurement.

Further details and embodiments of the invention emerge from FIG. 8. The figure shown there shows the essence of this invention.

A thin glass plate, possibly antireflection coated, carries one or more small insertion elements which can be pushed close to lenses, main objectives, etc. in such a way that they cause only partial—as a rule negligibly small—disturbances.

A preferred embodiment of the device according to the invention thus contains a device for the interference-free insertion of narrow bundles of rays into optical beam paths. For this purpose, optical insertion elements 4 are fastened to thin glass panes 41, which are inserted into the beam path directly upstream of lenses.

Figure 9:
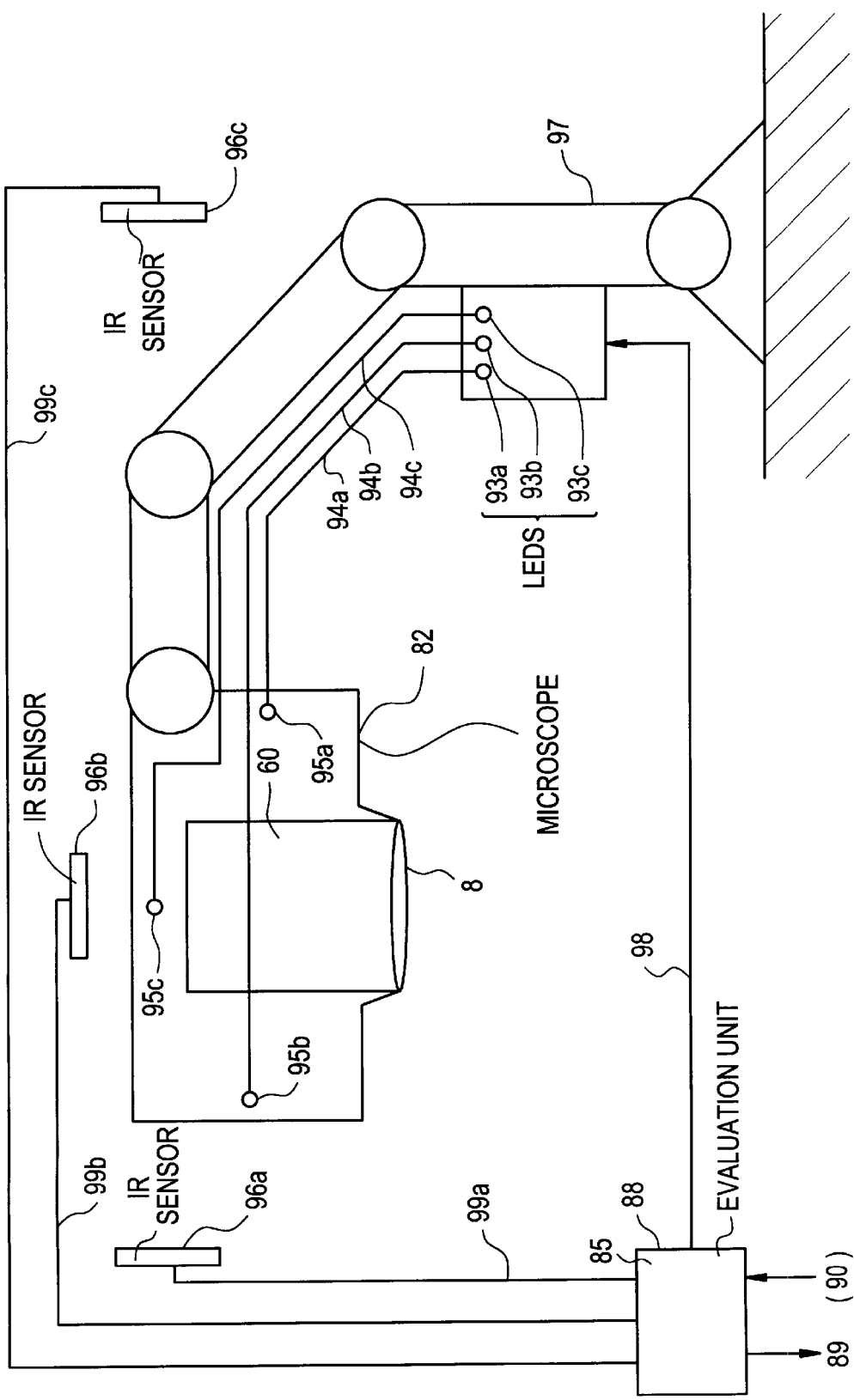
FIG. 9 shows a construction for registering the microscope position in space.
Figure 11:
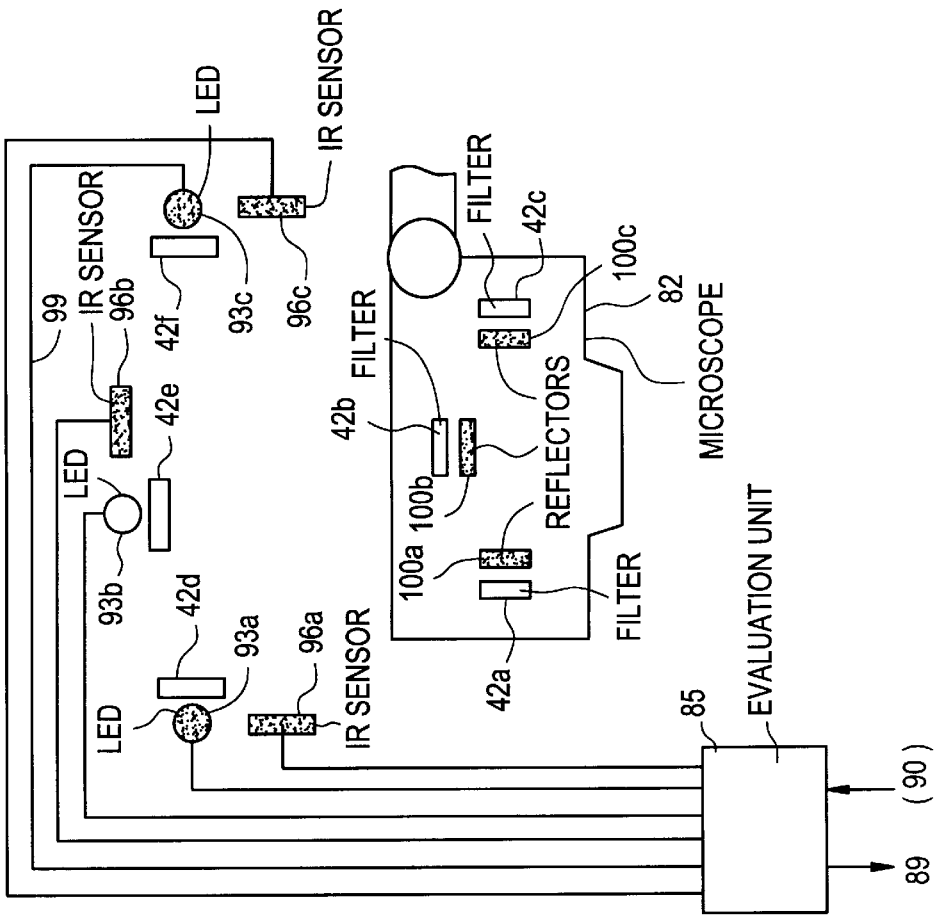
FIG. 11 shows a variant thereof.
Figure 10:
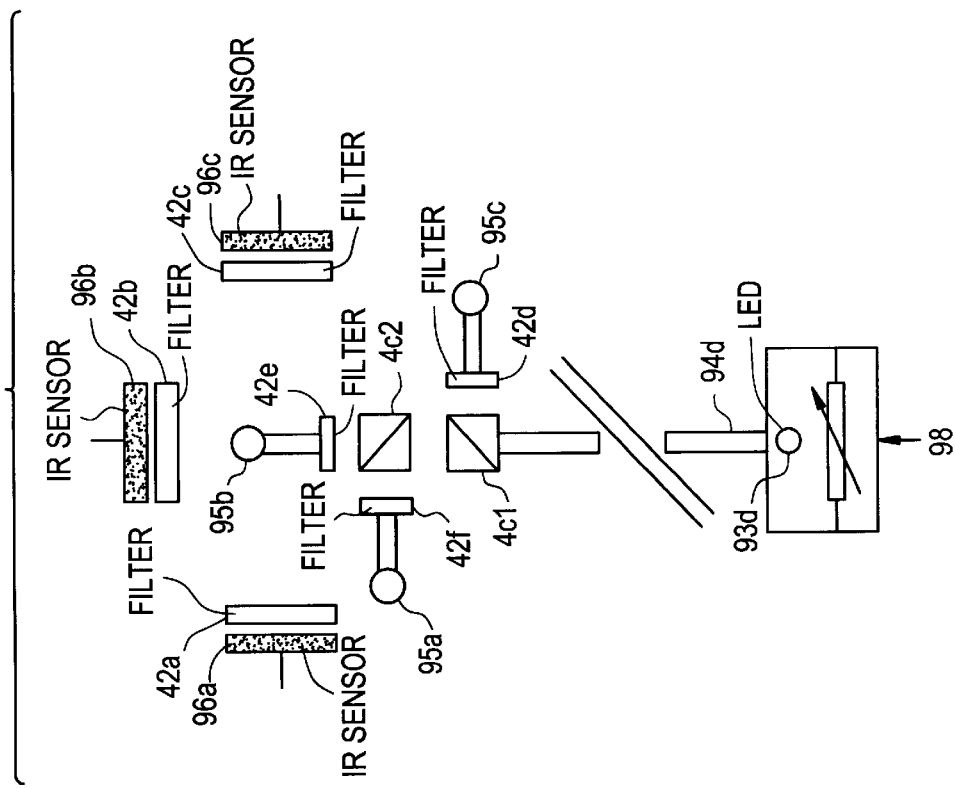
FIG. 10 shows a detail variant from FIG. 9.

A further preferred variant of the invention, which enables the position data of the measurement point to be determined absolutely in space, results from the use of an arrangement, which can also be used independently, in accordance with the features of at least one of FIGS. 9–11, respectively.

The position determination of the microscope is in this case undertaken in order to decide on the exact location of the operation field, observed through the microscope, from the setting data of the microscope (focus, zoom, etc.) with simultaneous knowledge of the position of a patient in space. This is becoming more and more important in modern microsurgery (stereotaxy), since a surgeon is thus enabled to find with great certainty the location at which the operation must be carried out. Conversely, it is possible in this manner to track precisely at which location the operation is being carried out. The significance of such knowledge is increasing with the advancing technology of making different diagnostic image data, for example X-ray, CT or MRI image data, visible in a microscope beam path, or superimposing them on the image seen, so that the surgeon can also make use of corresponding comparative information—shown correctly in terms of location.

The position determination of the microscope (in the sense of the invention, an endoscope can therefore also be meant) is carried out in accordance with the prior art using the various techniques. On the one hand there are microscope carrier frames which have measuring elements in their joints—similar to a robot arm from the machine industry—which continuously simultaneously track the position changes of the microscope and determine the respective position in space via a microprocessor. On the other hand, there are also microscopes and endoscope tips which determine the respective position with the aid of ultrasonic transmitters and sensors which are arranged on the microscope. In the case of endoscopes, operations are occasionally also carried out under a permanent X-ray beam, in order to be able to determine the position at least in an optically visible manner.

In the case of a novel development of the applicant, the ultrasonic technique is dispensed with and use is made of an infrared positioning system in which three infrared transmitters with encoded transmission signals are arranged on the microscope, the signals from which are detected by infrared receivers arranged in the operating theater. This technique allows a more exact position determination than by means of ultrasound, since primarily interfering influences can also be excluded and simultaneous working with ultrasonic devices—as may occur in the case of operations in the region of the brain—is not contraindicated.

In the case of all the previously known position determining methods, in spite of fundamental operational reliability of the methods, two problems have to be considered: the patient should not be influenced by the position determination and any measurement results in the area of the operation location should not be influenced by the position determining method.

These problems have not been satisfactorily solved. The specific refinement is therefore based on the object of providing a surgical microscope with a position determining system which influences neither the patient nor any measurement results from the area of the operation location (for example brain current measurements).

This object is achieved by means of using sound and current-independent position transmitters on the surgical microscope such as reflectors having specific reflection properties on the surgical microscope, by which the signals from a transmitter are detected by the receivers in a reflector-specific manner.

In this case, preference is given to the construction using infrared transmitters which, arranged remote from the surgical microscope, are excited by means of power, the light pulses emitted by them being conducted as far as the microscope by means of glass fibers, in order there to leave the glass fiber ends and—as in the case of the arrangement using IR light-emitting diodes on the microscope—to be registered by the sensors in the room and to enable a corresponding position determination.

Special embodiments of this variant primarily facilitate the reduction of the constructional size of surgical microscopes.

This arrangement thus leads to more compact surgical microscopes, whose position in space can be determined simply, without interfering ultrasonic signals, power flows or electromagnetic fields. It is thus possible for the surgeon to work in a more patient-friendly and more locationally precise manner.

Within the context of the invention, furthermore, there are various types of embodiment and variants thereof which result from the combination of the features mentioned here with features of the patent applications mentioned, which place other aspects of an inventive novel microscope under protection, said microscope preferably also being equipped precisely with the arrangement described above.

The principle of this variant is illustrated in FIG. 9: A plurality of peripherally arranged light-emitting emitting diodes 93 transmit encoded light pulses which are led to the microscope 82 via glass fiber lines 94. The light pulses emerge from the ends 95 of the glass fibers 94 and can thus be registered by IR sensors 96 arranged in the room. The incoming pulses are then fed via feedlines 99 and evaluated by an evaluation unit 85 and the position of the microscope 82 is determined in this way. The evaluation unit 85 is connected to a data conditioning unit 89 or, if appropriate, directly to a computer 90. The evaluation unit 85 may drive the light-emitting diodes 93 via a feedback connection 98. The microscope 82 contains an objective 8 and a beam path 60. It is held via a microscope stand 97.

In the variant according to FIG. 10, only the light from a single light-emitting diode 93d is used, which nevertheless emits light pulses alternately having different light colors. This is carried out, for example, by varying the feed voltage of the light-emitting diode 93d. Arranged at the microscope end of the glass fiber 94d are two beam splitters 4c1 and 4c2, which split the incoming bundle of light into three measuring bundles. These are in each case let through by suitable narrow band color filters 42 only to the associated glass fiber ends 95, by which means a spatial separation of the outgoing light pulses is possible.

Corresponding color filters 42 are connected upstream of the IR receptors 96, with the result that these also in each case respond only to the light pulses intended for them.

FIG. 11 shows a variant in which the glass fiber lines are dispensed with, in that both the light pulse transmitters 93 and the IR receptors 96 are arranged in the room and only reflectors 100, each having a quite characteristic reflection property for a specific light color, are fitted to the microscope 82, color filters 42 being connected upstream of said reflectors, with the result that only the corresponding light color is incident on them and can leave them once more. In a somewhat more complex evaluation method, the position determining unit 85 can in this way determine the position of the microscope.

It is of course also possible for the feedlines 99 to the IR receptors to be formed as glass fibers, in order that the room as a whole be intended to be subjected to less electromagnetic fields.

A preferred embodiment thus relates to an arrangement for determining the position of a surgical microscope 82 with the aid of frequent light pulses, which originate from the microscope 82 and are received by light receptors 96, glass fibers being arranged between light-emitting diodes 93 and the transmitting location 95 of the light pulses, so that the area of the microscope is free from interfering electric and electromagnetic waves.

A further preferred development of a device for carrying out the method according to the invention, which can also be used independently of the latter, comprises an arrangement for data processing for a microscope, for example a video microscope, provided that the latter is connected to an electronic data processing unit and/or a display.

The arrangement for data processing is in particular to be understood as any complete or modular device which is used in conjunction with a microscope or in conjunction with examinations carried out on a microscope in order to process data which are of significance for the operation or for the knowledge from the microscope or for the work under the microscope. The data processing unit is, for example, to be understood to include microprocessors, computers or work stations, with the aid of which, for example, data from the microscope can be registered, position data of the microscope can be registered and optionally further processed or forwarded, or with the aid of which the microscope is, for example, itself driven.

A display in the sense of the invention is to be understood to include, for example, monitor screens, cathode ray tubes, etc., on which information for a user can appear. Such displays can be arranged both outside the microscope, for example as a computer monitor screen, or else can be constructed as small displays which are connected to the optical beam path of the microscope such that a user obtains both an optical awareness from the optical beam path and also, simultaneously (superimposed), an optical awareness from the display.

In special cases, a display may also be understood to include in the widest sense an acoustic information device.

Video microscopes in the sense of the invention are microscopes having at least one optical beam path and at least one image recording device for the recording and display of an image, seen via the beam path, on a display. In recent times, video stereo microscopes, in which two parallel beam paths are provided and a 3 D image can be displayed on the display, have become a very frequent type of video microscope. Video microscopes are often used as surgical microscopes; all other microscopes and endoscopes which have the abovedescribed devices also lying within the context of the invention.

Above all in the case of surgical microscopes and, in particular, during an operation, a quantity of information accrues which may be of great significance for the surgeon. This is, for example, information about specific parameters of the microscope. However, this is also information about the position of the operation field being observed, information about the patient or his/her state of health or, respectively, his/her parameters such as pulse, blood pressure, blood oxygen content, etc. and, for example, also comparative data from earlier microscope recordings made via video or recordings from other recording methods such as X-ray, ultrasound, positron beam or MRI recordings.

In addition to this information, a quantity of control data also accrues which, for example, are output by the surgeon arbitrarily via control elements such as a computer mouse, foot switch, etc. to the data processing unit or to control elements for the microscope, in order to control the latter as required, for example to focus it.

Above all in the case of those applications where images are superimposed, be it optically or optoelectron-ically, for example by means of displays which are reflected via beam splitters into the eyepiece beam path, or purely electronically, for example by means of image processing and simultaneous representation of superimposed images on a display, a problem occurs in connection with the electronic data processing: during operations the surgeon relies on the one hand on a real time display and on the other hand on a rapid reaction of control elements of the microscope and on exact positioning of the microscope or its field of view.

In the case of conventional constructions, this means that enormously large computer powers are required of the data processing system. This computer power is used up by the recording and storage of data, conversion of the same into other data, conversion of data from analog values into digital values or vice versa, optional comparison of stored or parallel recorded data with recorded data and the output of data to control elements, displays, indicators, data networks and so on. At the same time, it is also necessary in the electronic data processing to load various software programs which make mutual interlinking necessary, which is often complicated and correspondingly expensive.

U.S. Pat. No. 5,073,857 describes a method and a device for a cell analysis which, inter alia, has a video camera, an image generator, a microprocessor, a counting device, a comparison device, a digital/analog converter, a control device for the microscope and a computer. The computer is in this case provided only as an extended input/output device for the microprocessor and the latter is assigned a program memory, with the result that it can be viewed for itself alone rather than as an actual computer which in turn requires the said high computer power in order to enable working in real time.

By contrast, the preferred development is based on the object of providing an arrangement for data processing or a microscope with such an arrangement in which it is possible to work with the most rapid processing times in real time and in which the required computer power in the data processing system itself can be kept small. In terms of software, too, it is intended to provide a compact construction with simple expansion capabilities.

This object is achieved by means of the application of the features described herein. This embodiment as a whole represents an arrangement which is comparable with a human; sense organs and extremities are connected via the spinal cord, which itself fulfills specific functions, with the brain (computer).

As a result of the arrangement according to the invention, all the data of interest are continuously and automatically conditioned in such a way that the connected computer (in many cases a work station) has access to optimum and standardized data formats which are determined and conditioned irrespective of its computer power. The computer does not have to carry out all the computing operations, as was previously the case; its EDP power can be restricted to the computing operations provided in each case to be calculated in its main memory, as a result of which it can itself be laid out in an optimum manner. The real time behavior required by the users can be achieved simply by means of the invention.

Particular embodiments of the arrangement. In the case of their application in the surgical microscope field, they primarily facilitate the mode of operation which is specific to the user in each case.

The arrangement according to the invention thus leads to microscopes or modes of operation using microscopes which are more compact, faster and more reliable for the user, which is primarily of enormous advantage in the field of microsurgery.

Within the context of the invention, furthermore, there are various types of embodiments and variants thereof which result from the combination of the features mentioned here with features of the patent applications mentioned, which place other aspects of an inventive novel microscope under protection, said microscope preferably also being equipped precisely with the arrangement described above. These are the patent applications: CH949/94-2, CH1525/94-0 and, in particular, CH1090/94-1.

Figure 12:
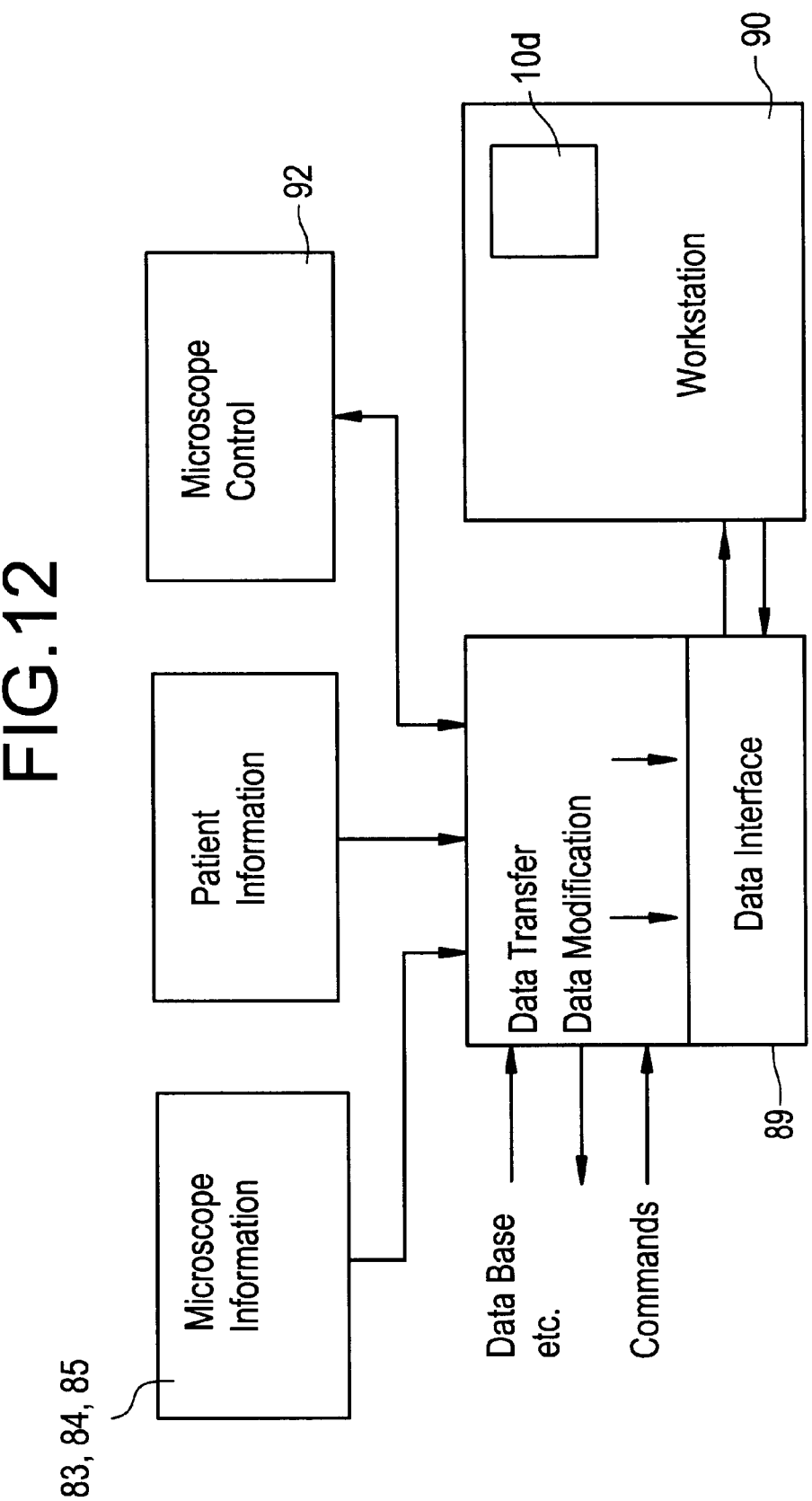
FIG. 12 shows a basic diagram of a construction in accordance with the invention and FIG. 13 shows a more detailed, self-explanatory basic diagram of a similar construction.
Figure 13:
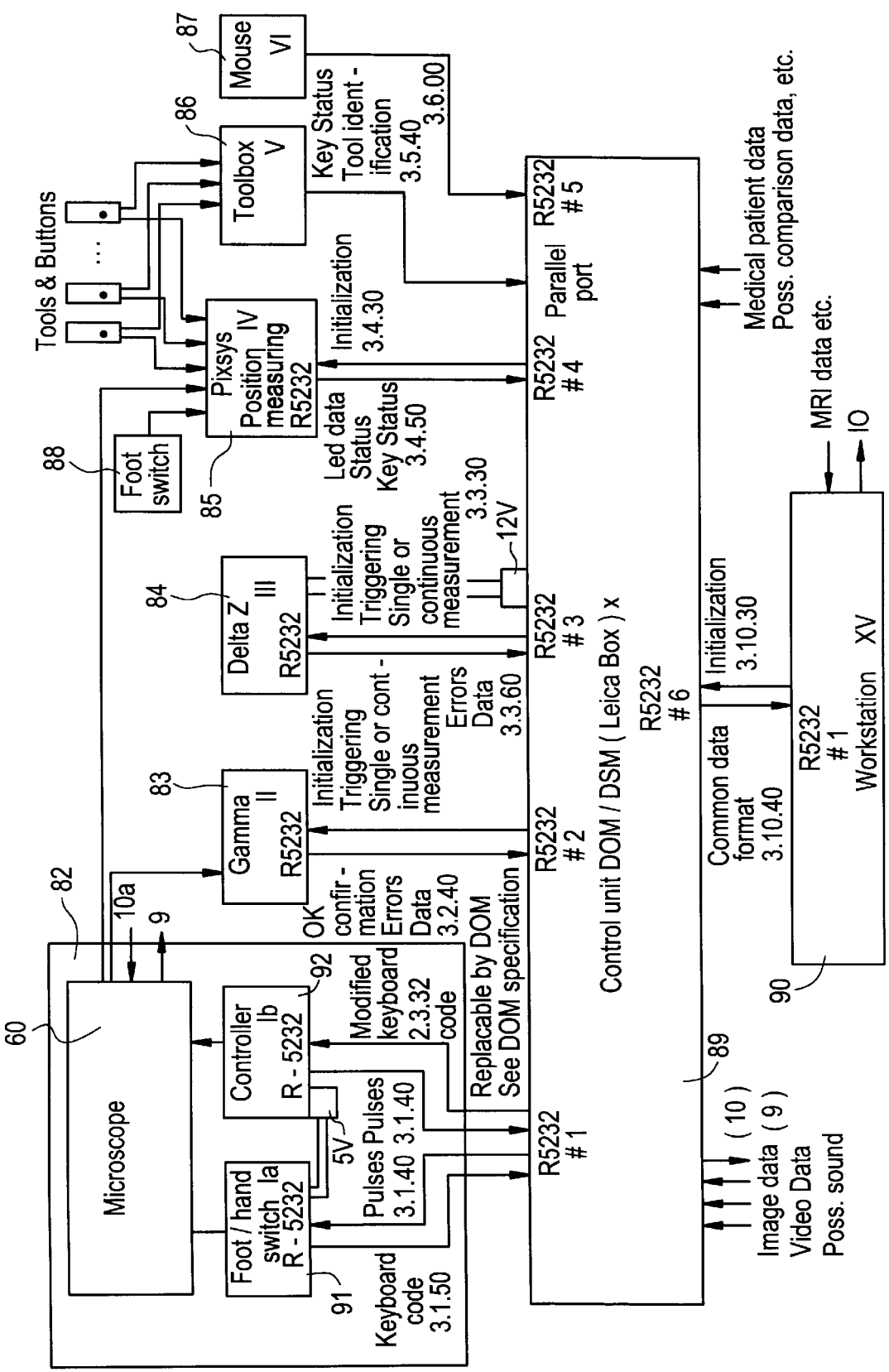

Further details and embodiments of the invention emerge from FIGS. 12 and 13.

The principle of this development is clarified in FIG. 12: a plurality of periphery devices are led together to a data conditioning unit 89 in order there to condition data for further processing in a computer 90. However, as required the data conditioning unit 89 also converts data from the computer 90 into such data formats as can be used immediately and directly in the peripheral devices. Specific data, whose processing in the work station is not necessary, can, if required, also be made directly available for other peripheral devices following their conditioning (conversion, format adaptation, linking with other data).

An example may be cited of a desired magnification which is reported by the user by instruction to the arrangement or to the data conditioning unit 89. The instruction, which is for example a numerical value, is compared with a measured value of the magnification from the device 85, this being initially, for example, an analog voltage value or a digital location vector value, which values are firstly automatically converted by the data conditioning unit 83 in order to make a comparison between the two desired and actual data items possible. If the comparison shows a difference, then, for example, a corresponding control value for the microscope control elements 92 is produced in order to enable a corresponding regulation in the manner of a control loop.

Also, for example, patient information data can be brought into view in visible form on a display, corresponding comparative data from a database also being displayed on the same display at the same time. Within the context of the invention, such data can, for example, also be conditioned without making any demand on the computer power of the computer 90. This is thus available for more complicated computing manipulations, for example for converting MRI image data for enlarging or diminishing the MRI image in accordance with the set magnification values in the microscope beam path 60 and for the image-processing superimposition of the MRI image on the image being viewed through the microscope beam path 60 and being recorded, for example by means of video camera 9, the completed superimposition being displayed for the user on a display 10a and/or 10b.

The statements in accordance with FIG. 13 are self-explanatory to those skilled in the art.

A microscope 82, which is connected to various peripheral devices such as device 83 for the automatic, electronically aided magnification measurement through the microscope optics 60, device 84 for the automatic, electronically aided distance measurement between the object being observed and microscope 82, device 85 for the automatic and electronically aided determination of the position of the microscope 82 in space, device 88 for driving position change drives of the microscope 82, database, video camera, device for registering patient data such as, for example, name, pulse, blood pressure, blood oxygen content, etc., is connected to a data conditioning unit 89 which conditions or converts data in the correct format before they go into a connected workstation or when they emerge therefrom, in order to enable real-time operation with relatively low computer powers in the work station.

List of Reference Symbols

This list of reference symbols also contains reference symbols from figures which are contained in the abovementioned Applications, since these reference symbols, or the features cited by means of these reference symbols and their corresponding description and drawing parts, count as simultaneously disclosed for combination purposes within the scope of this invention. In particular, this relates to the microscopes having specific beam paths and beam splitters and to the devices for measuring the magnification and the distance of the microscope from the object.

1 first beam path; a,b
2 second beam path (geometrically superimposed first beam paths); a,b
3 mechanooptical switching element
   3a–c opaque and preferably silvered aperture diaphragm
   3d LCD shutter element
   3e micromechanical lamellar mirror construction
   3f LCD alternating shutter element
4 beam splitter
   4a,b beam splitter
   4c beam splitter for splitting out measuring beam 4c1, 4c2
5 disk
   5a semicircular area
   5b remaining area of the disk 5
   5c circular segment areas
   5d
6 axis for disk
7 central axis
   7a,b central axis
8 main objective
   8a main objective
   8b main objective exchangeable with 8a (different focal lengths)
9 electronic image recording device
10 display
   10a display
11 mirror; a,b
12 positioning device; a–c
13 zoom
14 motor; a,b
15 reciprocating drive
16 feed line
17 light source
18 eyepiece
19 deflecting mirror
20 push rod
21 rigid mirror
22 object
   22a object detail
23 plane plate; a–d,a',b'
24 pivoting drive
25 linkage
30 lamellar mirror of 3e
31 tube lens
32 insertion element
   32a beam splitter
   32b mirror
   32c second insertion element
33 magnification optics
34 arrows
35 further mirror
36 actuating drive
37 beams
38 deflecting mirror; a,b
39 retro prism
40 balance weight
41 carrier plate a,b,c: prismatic with integrated mirror
42 color filter; a–f
43 interval switch
44 microprocessor
45 measuring array a
46 reference array a
47 image data transfer module
48 external image data input
49 servomotor for zoom 13; a,b 50 connecting lines a–g
51 magnification indicator a–c
52 cam disc
53 coupling
   53a between servomotor 49b and zoom 13 and/or between 49 and 52
   53b between cam disk 52 and magnification indicator 51b
54 mechanical pick-off
55 pointer; a,b
56 laser
57 measuring beam a–c, c1
58 reference beam
59 arrows for displaceability of the insertion element 32
60 microscope beam path a–e
61 first deflecting element a
62 focusing element a,b
63 optical fiber end piece a,b
64 light source a
65 second deflecting element
66 sensor
67 distance range a
68 connecting line
69 distance measuring system
70 connection
71 magnification measuring unit
72 position determining system a,b
73 interferometer
74 semitransparent mirror
75 reflector
76 detector
77 electromechanical positioning element
78 interferometer control
79 grating
80 detector CCD
81 stages
82 microscope
83 arrangement for measuring the magnification of the microscope
84 arrangement for measuring the distance between object and microscope
85 position measuring system for determining the absolute position of the microscope in space in order also to be able to infer therefrom the position of the field of view on the object in accordance with knowledge of the distance
86 toolbox for various user programs
87 command control element (computer mouse)
88 command control element for movement control of the microscope (e.g. foot switch)
89 data conditioning unit
90 computer (workstation)
91 control switch for microscope
92 electromechanical control unit for microscope (zoom, focus etc.)
93 light-emitting diodes; a–c
94 glass fibers; a–c
95 ends of the glass fibers; a–c
96 IR receptors; a–c
97 microscope stand
98 feedback
99 feed lines; a–c
100 reflectors with special surface
b spacing between the measuring beams 57a and 57b
b' spacing between the measuring beams 57a and 57b at the measuring array
d1,2 stereo base

We claim:

1. A method of determining position data of a measurement point on an object being observed through a microscope, in which position data of the microscope and data about a focal plane and a magnification data of the microscope are determined and position data are subsequently calculated therefrom, wherein the magnification data are measured directly with the aid of at least one optical measuring beam (57a, 57b), which comes from outside and is inserted at least into zoom optics (13) of the microscope and passes through the latter, from deflection of the measuring beam (57a, 57b) and inserted into a calculation for determining position data.

2. A method according to claim 1, wherein measurement is carried out by means of optical deflection of at least one visible measuring beam (57) by microscope optics (8,13), the measuring beam (57a) lying in the visible wavelength range and the measuring beam (57a) being assigned a measuring scale (51c) which is visible to an observer and on which the observer can read the magnification value directly.

3. A method according to claim 1 wherein measurement is carried out by means of optical deflection of at least one measuring beam by microscope optics (8,13) onto a mechanically defined optoelectronic location-resolving measuring array (45) whose electronic output values correspond to the magnification.

4. A method according to claim 1, wherein measurement is carried out by optical deflection of two measuring beams (57a,b) located at specific angles to an optical axis (7) of the microscope by microscope optics (8,13) onto an optoelectronic measuring array (45b), whose spacing (b) is known, the spacing (b') of the deflected beams (57a,b) from each other or the electronic output values resulting therefrom corresponding to the magnification.

5. A device for measuring the magnification in an optical beam path (7) in a microscope having microscope optics (8,13), having at least one laser (56) for producing at least one measuring beam (57) and at least one magnification indicator wherein connected downstream of the laser (56) at least one insertion element (32) is provided via which the measuring beam (57) can be steered through the microscope optics (8,13), and connected downstream of the microscope optics (8,13) at least one calibrated magnification indicator (51c) is provided on which the magnification may be read or at least one beam splitter (4) is provided, on which the magnification can be read off or at which the measuring beam (57) can be split off and fed to a measuring array (45), electronic output values from the measuring array (45) corresponding to the magnification.

6. A device as claimed in claim 5, wherein the measuring beam (57) is split by an insertion element (32a), which is a beam splitter, into two measuring beams (57a,b), which are reflected via the insertion element (32a) and via a second insertion element (32c) into the beam path of the microscope and, via the beam splitter (4c), onto the measuring array (45b), the spacing (b) between the two measuring beams (57a,b) being defined and the spacing (b') between two measuring beams (57a,b) at the measuring array (45b) corresponding to the magnification.

7. A device according to claim 5, characterized in that the insertion element or elements (32) are arranged or constructed on a flat, transparent carrier plate (41a) which is built into the beam path—if appropriate, interchangeably—parallel to the main objective plane and upstream of the main objective.

8. A device according to claim 5, characterized in that the measuring beam (57) can be produced in a laser (56) whose wavelength lies in the invisible range and whose output power lies below an intensity which is damaging to the human eye, and/or in that—considered in the direction of the measuring beam through the main objective—a color filter is arranged downstream of the beam splitter (4c) for splitting off the measuring beam, a very narrow band filter effect of said color filter filtering out the color frequency of the measuring beam.

9. Device according to claim 5, characterized in that the measuring beam (57) can be output in a cyclic manner intermittently and/or using the measuring array (45) and, if appropriate, using other opto-electronic or electromechanical components of the microscope.

10. Device according to claim 5, characterized in that the magnification value of the microscope optics which is determined at the measuring array (45a) is fed back or displayed via a display (10b) in a form suitable for an observer, the display (10b) making use of that same beam splitter (4c) for splitting out the measuring beam (57a) for inserting the display image.

11. Device according to claim 5, characterized in that the image of a display can be inserted into the observation beam path via the beam splitter (4c) for the measuring beam (57), the display (10b) being coupled for this purpose to a module (47) for image data transmission, which is further connected via a microprocessor (44b) to the measuring array (45a) and, makes available image data, adapted in accordance with magnification, from other image data sources (48).

12. A device as claimed in claim 5, wherein at least the beam splitter (4c) for splitting out the measuring beam (57) is constructed as a mechanooptical switching element whose switching state alternates between a transmissive and a reflective state.

13. Device according to claim 6, characterized in that small optical insertion elements (for example beam splitters) (4) are arranged or constructed on a thin carrier disk (41), which is inserted into the beam path.

14. Device according to claim 13, characterized in that the carrier plate (41) is arranged in the direct vicinity of objectives or lenses.

15. A device as claimed in claim 13, wherein the optical insertion elements (4) are arranged in the beam path of a surgical microscope.

16. A device according to claim 8, wherein said color filter is a Fabry-Perot filter.

* * * * *